United States Patent [19]
Yager et al.

[11] Patent Number: 6,110,339
[45] Date of Patent: Aug. 29, 2000

[54] NANOFABRICATED SEPARATION MATRIX FOR ANALYSIS OF BIOPOLYMERS AND METHODS OF MAKING AND USING SAME

[75] Inventors: Thomas D. Yager, Mississauga; Paul Waterhouse, Copetown; Alexandre M. Izmailov, Toronto; Bruno Maruzzo, Toronto; John K. Stevens, Toronto, all of Canada; Marina T. Larson, Yorktown Heights, N.Y.

[73] Assignee: Visible Genetics Inc., Toronto, Canada

[21] Appl. No.: 08/973,932

[22] PCT Filed: Jun. 7, 1996

[86] PCT No.: PCT/US96/09999

§ 371 Date: Dec. 16, 1997

§ 102(e) Date: Dec. 16, 1997

[87] PCT Pub. No.: WO96/42012

PCT Pub. Date: Dec. 27, 1996

Related U.S. Application Data

[60] Provisional application No. 60/000,036, Jun. 8, 1995.

[51] Int. Cl.[7] .................................................. G01N 27/447
[52] U.S. Cl. .......................... 204/451; 204/453; 204/601; 204/604; 435/6; 435/287.2; 436/94
[58] Field of Search ..................................... 204/450–456, 204/601, 606; 422/101, 68.1; 435/6, 287.2, 288.6, 288.7; 436/89.94; 210/198.2, 198.3

[56] References Cited

U.S. PATENT DOCUMENTS

| | | |
|---|---|---|
| 5,135,627 | 8/1992 | Soane . |
| 5,340,452 | 8/1994 | Brenner et al. ...................... 204/180.1 |
| 5,593,838 | 1/1997 | Zanzucchi et al. .......................... 435/6 |
| 5,814,201 | 9/1998 | Simpson et al. ......................... 204/614 |
| 5,928,880 | 7/1999 | Wilding et al. ........................ 435/7.21 |

FOREIGN PATENT DOCUMENTS

| | | |
|---|---|---|
| 0 335 703 | 10/1989 | European Pat. Off. . |
| 0 391 674 | 10/1990 | European Pat. Off. . |
| 0 500 211 | 8/1992 | European Pat. Off. . |
| 0 653 631 | 5/1995 | European Pat. Off. . |
| 3-167468 | 7/1991 | Japan .................................... 204/614 |
| WO91/12904 | 9/1991 | WIPO . |
| WO93/00986 | 1/1993 | WIPO . |
| WO96/35810 | 11/1996 | WIPO . |

OTHER PUBLICATIONS

Tanaka, n., et al, "Starburst Dendrimers as Carriers in Electrokinetic Chromatography", Chemistry Letters, pp. 959–962, 1992.

Zimmerman, S.C., et al, "Self–Assembling Dendrimers", Science, 271:1095–1098, Feb. 23, 1996.

Volkmuth, W.D. and R.H. Austin, "DNA electrophoresis in microlithographic arrays", Nature 358:600, 602, Aug. 1992.

Volkmuth, W.D., et al, "Trapping of branched DNA in microfabricated structures", Proc. Natl. Acad. Sci. USA 92:6887–6891, Jul. 1995.

*Primary Examiner*—William H. Beisner
*Attorney, Agent, or Firm*—Oppedahl & Larson LLP

[57] ABSTRACT

Separation matrices useful in the formation of solid-state mm- to cm-scale devices for the rapid, high-resolution separation of single-stranded DNA ladder bands generated by the Sanger dideoxy- or Maxam/Gilbert chemical DNA sequencing procedures are formed from a solid support (1) having a plurality of posts (4) disposed on a first major surface thereof to form an obstacle course of posts (4) and pores (5). The posts are arranged in a regular X, Y array and are separated one from another by a distance of 100 nm or less, preferably 10 to 30 nm, and are optionally separated into lanes 2. The separation matrix can be manufactured by first forming a mold, preferably a reusable mold using lithography techniques. The mold is the reverse of the desired pattern of posts and pores of the obstacle course, and is used for casting the obstacle course. The cast obstacle course is then fused to a solid support and separated from the mold. Alternatively, the separation matrix can be formed from a polymer which undergoes specific and quantifiable swelling in the presence of a selected chemical compound. In this case, the matrix is cast on a mold in a conventional manner with a spacing between posts greater than the desired final spacing of 100 nm or less. For use, a buffer solution saturated with the specific chemical agent that controls swelling is added, causing the posts to swell to a defined amount to achieve the desired separation.

22 Claims, 5 Drawing Sheets

NANOFABRICATED SEPARATION MATRIX FOR ANALYSIS OF BIOPOLYMERS AND METHODS OF MAKING AND USING SAME

This application claims priority from U.S. Provisional Application Ser. No. 60/000,036 filed Jun. 8, 1995.

BACKGROUND OF THE INVENTION

This application relates to a novel form of separation matrix for the analysis of biopolymers, particularly nucleic acid polymers.

The use of separation matrices for the analysis of biopolymers is well established. For example, agarose gels, polyacrylamide gel and other types of gel matrices are used routinely to separate proteins, polypeptides and polynucieotides into subclasses based upon properties such as size, weight and molecular charge. Analysis of the separated subclasses is used to identify and characterize proteins, to detect and characterize mutant forms of proteins, and to detect and characterize polynucleotides. For example, analysis of separated polynucieotide fragments is a basic part of the process for most determinations of nucleic acid sequence.

Although the gel matrices which have been used for these separations to date are effective and can produce useful analytical results, they are not without their deficiencies. These deficiencies include (1) a randomness of structure, and (2) a requirement for continuous hydration after formation. Both of these deficiencies can lead to unpredictable variations in the results obtained between one gel and another, whether as a result of intrinsic variations in the gels, or as a result of changes resulting from differing storage conditions. In addition, the micro-inhomogeneity resulting from randomness of the gel structure reduces the actual resolving power of the gels. A further deficiency of known gels used in separations of biopolymers arises from the nature of the gel materials themselves. The materials used may be subject to breakdown by high electric fields, thus limiting the field strength that could otherwise be employed to obtain more rapid separation. In addition, the gel, or materials used in forming the gel such as accelerators, may interfere with optical detection of the separated biopolymers.

Volkmuth et al, *Nature* 358: 600–602 (1992) have proposed the use of a $SiO_2$ obstacle course fabricated using optical microlithography for the analysis of large DNA molecules having a length on the order of 100 kilobases. The obstacle course is made up of a regular array of posts having separations of 1 $\mu$m between the posts. DNA loaded onto the array was separated by size by the application of an electric field, and detected using epifluorescence microscopy.

The obstacle course described by Volkmuth et al. is not well-suited for use in diagnostic applications, however, because the total length of the DNA fragments in most diagnostic DNA sequencing applications, diagnostic RFLP (restriction fragment length polymorphism) procedures, and the like is between about 20 and 300 to 400 nucleotides. As such, the looping of long strands of DNA observed by Volkmuth cannot be relied upon as a basis for separation. Furthermore, the fabrication process of Volkmuth et al. uses electron beam lithography to make each individual device, which would be prohibitively expensive for diagnostic applications.

International Patent Publication No. WO94/29707 discloses a microlithographic array for macromolecule and cell fractionation. The array is made using photolithography and then used for separation of macromolecules or cells migrating under the influence of an electric, magnetic, hydrodynamic or optical field.

It is an object of the present invention to provide an alternative from of separation matrix which overcomes these deficiencies of known gel matrices and which is useful in the analysis of smaller DNA fragments useful in diagnostic applications.

It is a further object of the present invention to provide a separation matrix for the separation and analysis of biopolymers which has a highly regular structure.

It is still a further object of the present invention to provide a separation matrix which can withstand very high electric field strengths.

It is still a further object of the present invention to provide a separation matrix which permits separated biopolymers to be optically detected with very high efficiency.

It is still a further object of the invention to provide a method for manufacturing the novel separation matrices of the invention.

It is still a further object of the present invention to provide a method for separating biopolymers, and in particular for separating oligonucleotide fragments for purposes of analyzing DNA sequences, using the novel separation matrices of the invention.

SUMMARY OF THE INVENTION

The present invention provides a separation matrix useful in the formation of solid-state mm- to cm-scale devices for the rapid, high-resolution separation of single-stranded DNA ladder bands generated by the Sanger dideoxy- or Maxam/Gilbert chemical DNA sequencing procedures. Such device are referred to herein as "DNA Sequencing Chips."

The separation matrix comprises a solid support having a plurality of posts disposed on a first major surface thereof to form an obstacle course of posts and pores. The posts are arranged in a regular X,Y array and are separated one from another by a distance of 100 nm or less, preferably 10 to 30 nm.

The separation matrix of the invention can be manufactured by first forming a mold, preferably a reusable mold using lithography techniques. The mold is the reverse of the desired pattern of posts and pores of the obstacle course, and is used for casting the obstacle course. The cast obstacle course is then fused to a solid support and separated from the mold.

Alternatively, the separation matrix can be formed from a polymer which undergoes specific and quantifiable swelling in the presence of a selected chemical compound. In this case, the matrix is cast on a mold in a conventional manner with a spacing between posts greater than the desired final spacing of 100 um or less. For use, a buffer solution saturated with the specific chemical agent that controls swelling is added, causing the posts to swell to a defined amount to achieve the desired separation.

DETAILED DESCRIPTION OF THE INVENTION

Figure 1A:
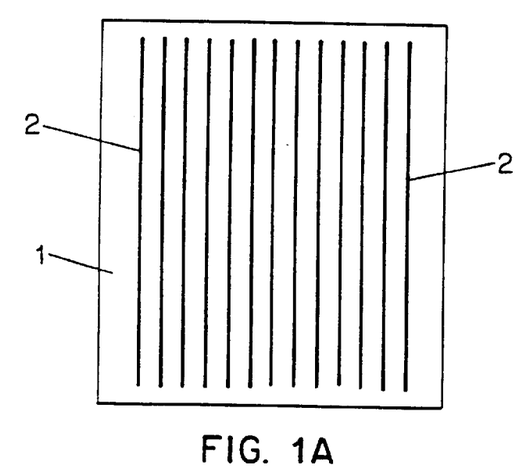
FIGS. 1A, 1B and 1C shows a nanofabricated separation matrix according to the present invention.
Figure 1B:
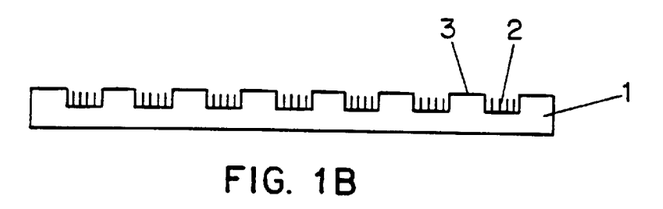

FIG. 1A shows a separation matrix according to the present invention. As shown, the separation matrix has a solid support 1 on which are disposed a plurality of lanes 2. In the embodiment shown in FIG. 1A, each lane 2 is approximately 10 µm wide and 1 µm or less deep, and is separated from neighboring lanes by a separator 3 of approximately 10 µm in width. (FIG. 1B) The width of each lane, and indeed the use of separated lanes at all is a matter of design choice and is not critical to the invention, although it should be noted that lane separation allows each lane to act as a separate capillary. It will be appreciated, however, that the sizes noted above provide for the possibility of 50 lanes in a 1 mm wide chip, which allows for very high throughput in a small area.

Figure 1C:
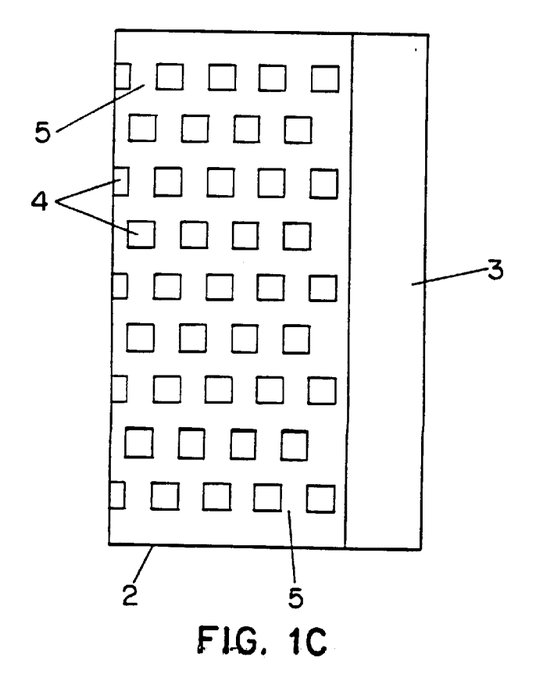

Each lane 2 contains a plurality of posts 4 which form an obstacle course for the separation of the biopolymers as shown in the partial top view of one lane 2 and separator 3 in FIG. 1C. The posts 4 are disposed in a regular pattern leavings pores 5 open for the passage of materials through the separation matrix. The spacing between the posts 4 must be large enough to permit passage of the biopolymer to be separated, yet small enough to provide an obstacle to passage which will result in separation. The determination of the appropriate size requires a consideration of many factors, including the overall size of the device, the degree of separation to be achieved by the device, and the size of the polymers to be separated. Each line of posts 4 may be in alignment with or offset with respect to adjacent lines of posts. It may be advantageous to form the separation matrix such that the spacing between lines of posts is sufficient to allow migrating molecules to reassume a random distribution of orientations. If spacing is finer, and DNA does not achieve random reorientation, reptation behavior result. This would be a different mode of electrophoresis, which may have useful properties as well.

Figure 2:
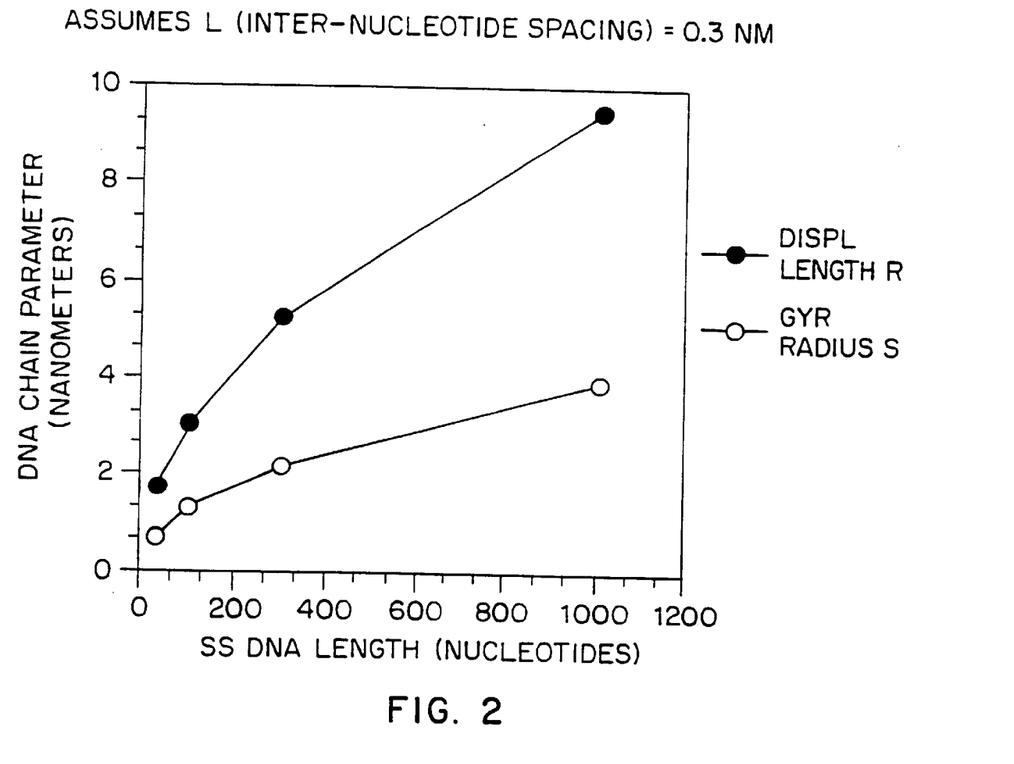
FIG. 2 shows calculated values for DNA chain parameters R and S as a function of oligonucleotide fragment length, assuming a distance L=0.3 nm for adjacent nucleotide residues.

As a matter of first principle, the appropriate size for the pores 5 between the posts 4 can be determined empirically, i.e., by testing a series of spacings to determine the effectiveness of each for separation of biopolymeric materials of a given size range, or it can be determined theoretically based upon the properties of the polymer in question. For example, single-stranded DNA in a denaturing solvent is linear polymer with a random-coil configuration. For such a polymer, several statistical measures of the chain geometry can be defined. The displacement length R is defined as the root-mean-square distance between the two terminal groups of the chain. This parameter is directly related to the radius of gyration S, which is defined as the root-mean-square distance of element i within the polymer from the center of gravity of the polymer. According to the derivation given by Flory in 1953, for a linear polymer in a random-coil configuration, $$R=L*(N)^{1/2}$$

and $$S+2.45*R$$

where N is the number of elements in the chain, (i.e., the number of nucleotide residues in a single-stranded oligonucleotide fragment) and L is the distance between centers of adjacent elements in the chain. FIG. 2 shows calculated values for R and S as a function of fragment length, assuming a distance L=0.3 nm for adjacent nucleotide residues.

To use this information to determine the appropriate spacing for a separation matrix, it is necessary to understand how these parameters are associated with the movement of a polymer through an obstacle course. Several recent papers in polymer theory have considered the diffusion of a random coil through a fixed course of obstacles, both in the presence and absence of a motive force (e.g. an electrophoretic field). The general conclusion from these studies is that a spacing between obstacles that is of the same order of magnitude as the displacement length R or the gyration radius S a polymer will impose entropic barriers to the movement of that polymer though the obstacles. This is the case because the polymer chain will have to transiently adopt a conformation of low entropy which is thermodynamically disfavored to move through the gap.

Applying this conclusion to the separation of oligonucleotide fragments used in sequencing, we have assumed that single-stranded fragments of interest may have a size in a range from 30 to 1,000 nucleotides. This corresponds to an R value between 1.6 and 10 nm. Therefore, as a first approximation, a spacing between obstacles of 1 to 10 nm should be effective for achieving separation of such fragments. This size range is consistent with the median pore radius of 0.5 to 4 nm observed for polyacrylamide gels. Of course, larger spacings will still lead to separation, although with less efficiency than if a smaller spacing is used, and will be more easily manufactured. Thus, in accordance with one aspect of the present invention, the spacing between the posts is advantageously less than 100 nm, preferably 1 to 30 nm. Larger spacing between the posts may be particularly useful in a hybrid obstacle course as discussed more fully below.

Separation matrices according to the invention can be manufactured using electron beam lithography to form a mold which is the reverse of the desired pattern of posts and pores making up the obstacle course, casting the obstacle course in the mask, and then fusing the cast obstacle course to a solid support for stripping from the mold. Preferably, the mold is reusable.

Figure 3:
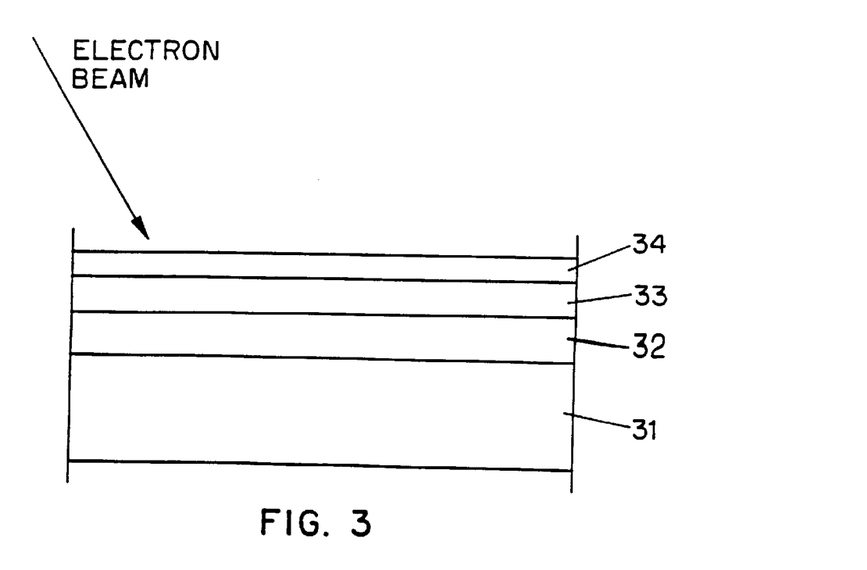
FIG. 3 shows a layered composite useful for forming a mold to make the separation matrix of the invention.

To form the mold, a substrate is coated with a pattern receiving layer or layers. For example, as shown schematically in FIG. 3, a tungsten substrate 31 which will ultimately form the mold, may be coated with a thin layer of a dielectric such as silicon dioxide 32, a thin layer of a low cross-section, highly conductive metal, such as aluminum 33, and a layer of an electron sensitive resist 34. Preferred resists are positive resists such as polymethylmethacrylate derivatives, since these will in general provide the highest resolution. Cowie, J. M. G. Polymers: *Chemistry and Physics of Modern Materials*, 2nd ed. Blackie, London, (1991). The resist layer is preferably deposited by spray deposition, although formation of a Langmuir/Blodgett film on water, followed by transfer to a solid surface can also be used for the formation of molds with resolution on the order of 50 to 80 nm. Miyashita et al., *Prog. Polymer Sci.* 18: 263–294 (1993).

The coated substrate is positioned on the stage of an electron beam lithography tool having appropriate resolution to draw lines of the dimensions desired. Suitable tools for this purpose include the JEOL JBX-5DII(U) electron beam tool (resolution of 20 nm) and the Leica/Cambridge EBMF 10/5 CS electron beam lithographic instrument (resolution 150 nm). The electron beam is used to write a pattern in the resist which is either a positive image (in the case of a positive resist which hardens to resist removal when exposed to the electron beam) or a negative image (in the case of a negative resist which becomes removable when exposed to the electron beam) of the posts and pores of the desired obstacle course. The exposed resist is then developed, to leave the patterned mask on the substrate.

Once the mask has been formed, the next step is the transfer of the pattern down through the layers of the substrate using successive treatments with specific chemical etchants, culminating in the etching of the substrate itself to produce a reusable mold for use in forming the separation matrix of the invention.

The separation matrix of the invention can be made of any of a number of materials, and the manner of forming the matrix within the mold will depend to a large extent on the nature of the material selected. For example, separation matrices made from silicon dioxide or similar materials can be formed using a chemical vapor deposition process to deposit material within the mold. Thereafter a glass base can be fused to the deposited materials, for example using the technique of field assisted silicon glass fusion (Wallis et al., *J. Appl. Phys.* 40: 3946–3949 (1969)) to increase the dimensional stability of the molded matrix and to facilitate its separation from the mold.

The matrix may also be formed from a variety of polymeric materials, including polymethylmethacrylate, ultraviolet-curable polyurethanes, ultraviolet-curable epoxies and other polymers with suitable physical and chemical properties, i.e., optical transparency and low fluorescence at relevant wavelengths, thermal conductivity and lack of electric charge. These materials can be formed into the obstacle course relying on capillarity as in the techniques of polymer casting (Kim et al, *Nature* 376: 581–584 (1995), and then cured either chemically or photochemically.

A mold as described above can also be used to form the separation matrix of the invention using the technique of imprint lithography as described by Chou et al., *Science* 272: 85–87 (1996). In this technique, a thin layer of a polymer resist such as polymethylmethacrylate is applied to a substrate. The polymer resist is then softened to a gel by heating it to a temperature above its glass transition temperature, and the mold is pressed against the softened resist to form a thickness contrast pattern. The mold is then removed and an anisotropic etching process such as reactive ion etching or wet etching is used to remove the resist from the compressed areas.

In the case of swellable polymers, larger starting molds can be used because the unswelled spacing between the posts is greater, and thus presents less of a challenge in terms of molding and separation technology. Molds for this purpose can be made by ultraviolet light-based lithographic techniques because less resolution is needed. In this case, the key is to determine the maximum amount which a given polymer will swell when in the presence of a saturating amount of the swelling control agent, and then making the posts in a size such that when this amount of swelling occurs, the desired final dimensions are achieved.

Suitable swellable polymers useful in the present invention are insoluble cross-linked polymers which are modified to have a specific affinity for a non-DNA material. Such polymers include polyvinylalcohol, polyethyleneimine, polyacrylamide, polystyrene, cross-linked dextran, and polyacrylic acid. Modifiers are selected to provide appropriate specificity to the polymer such that the amount of swelling can be controlled by addition of a selected agent. By including a saturating amount of the selected agent in the electrophoresis buffer, the degree of swelling of the polymer matrix can be consistently maintained, even after cycles of dehydration and rehydration. Synthesis of polymers of this type are described in the literature, including in International Patent Publication No. PCT/US91/12626 which is incorporated herein by reference.

After the obstacle course is formed, it is placed on a solid support which will form a part of the final separation matrix, providing dimensional stability to the final product and to the obstacle course during separation from the mold. Suitable materials for the solid support include fine quartz or pyrex cover slips which can be fused to posts of silicon dioxide and similar materials by field-assisted silicon glass fusion. Wallis et al. *J Appl. Phys.* 40: 3946–3949 (1969).

After the solid support is fused to the posts of the obstacle course, the separation matrix (support and posts) is separated from the mold. At this stage, the separation matrix of the invention can be used for separation of biopolymers by filling the matrix with a buffer solution, placing opposing ends of the matrix in contact with solution electrodes, loading a sample at one end of the separation matrix, applying an electric field between the solution electrodes and detecting separated oligonucleotide fragments at the other end of the separation matrix. There are various nuances which can be employed, however, to improve the versatility and utility of the separation matrix of the invention.

Figure 4:
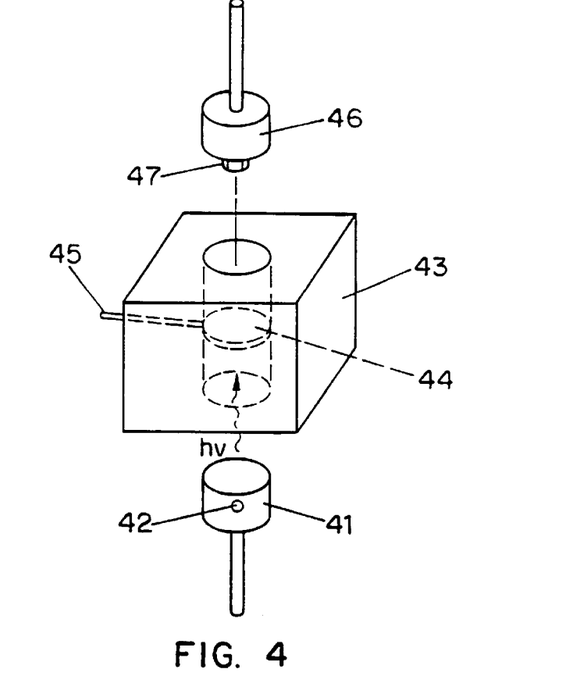
FIG. 4 shows an apparatus for manufacturing separation matrices.

FIG. 4 shows an apparatus suitable for forming multiple replicate copies of a DNA sequencing chip, using a mold and a photopolymerizable material using the procedures discussed above. As shown, a moveable base 41 having a lamp 42 for delivering light suitable for inducing photopolymerization positioned therein is disposed within a housing 43. The base 41 supports a chemically treated glass cover slip or other substrate 44 in alignment with an injection port 45 in the housing. Monomer or prepolymer solution is injected through the injection port 45 onto the top of the substrate 44. A piston 46 having the mold 47 for the pattern of plugs and pores is then pressed down into the solution on top of the substrate 44. The lamp 42 is then turned on to polymerize the solution in the mold, after which the molded polymer is separated from the mold 47 and the housing 43 by raising the piston 46 and lowering the base 41.

A modified version of the device of FIG. 4 could instead be used to repetitively make multiple copies of a DNA sequencing chip by imprint lithography. In this case, instead of a monomer or prepolymer solution, a polymeric sheet would be used as the starting materials. This would be heated above the glass transition temperature and then piston 46 having mold 47 would be pressed down into the softened polymeric sheet to make the replica. The temperature would be lowered again below the glass transition point and then piston 46 and mold 47 would be removed. Instead of lamp 42, this apparatus would have a heating element.

In addition to the posts making up the separation matrix, DNA Sequencing Chips in accordance with the invention include electrodes deposited on a bottom or top substrate to generate an electric field to induce migration of materials in the matrix. This can be a simple pair of electrode disposed at opposing ends of the separation matrix to impose an electric field in one direction on materials within the separation matrix. Preferably, however, an extended series of micro-electrodes is disposed on the substrate, multiple electrodes within each lane of the device.

Figure 5:
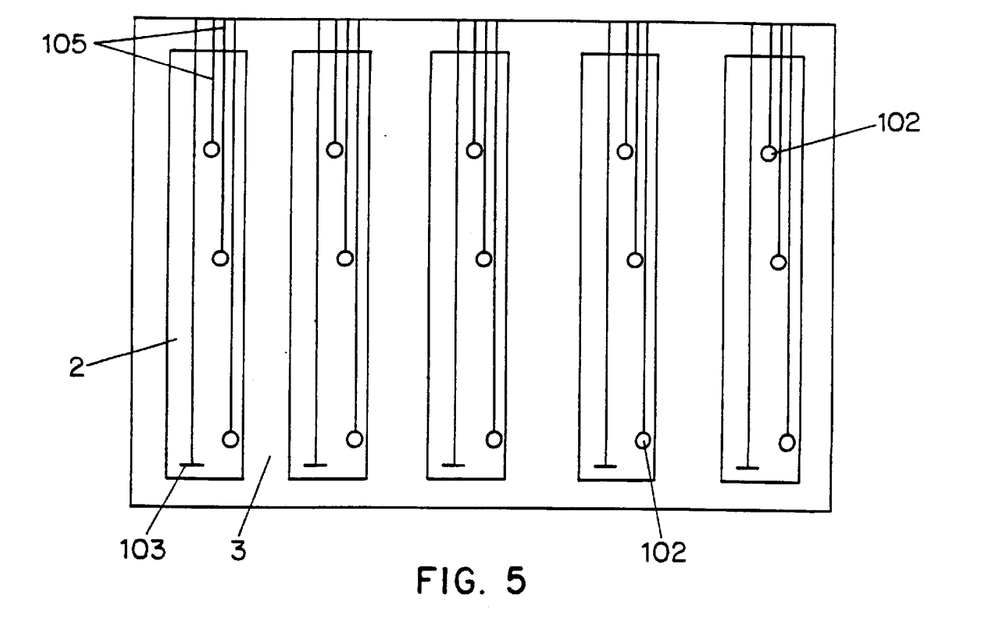
FIG. 5 shows a layout of electrodes useful in the invention.
Figure 6:
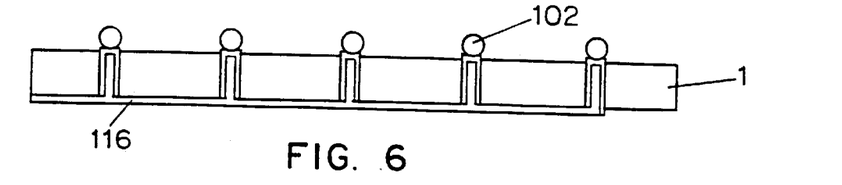
FIG. 6 shows a layout of electrodes useful in the invention.

FIG. 5 illustrates one arrangement of micro-electrodes and conducting wires on the substrate with posts and pores omitted for clarity. The micro-cathodes, 102, and micro-anodes, 103, are deposited in the lanes 2. Conducting leads 105 can be formed directly across the substrate 101 or if micro-holes are cut through the substrate, it is possible to construct the wire connections, 116, on the underside of the substrate 1, as illustrated in FIG. 6. The micro-electrodes and leads may be compositions of any relatively high conductance materials. Preferably the electrodes will be made of a coated or corrosion resistant material such as the noble metals platinum or gold. Corrosion resistance sufficient to withstand exposure to the buffer system employed in the separation is required, although noble metals are not necessary if the device is disposable.

The pattern of the micro-electrodes on the substrate may be chosen according to the demands of the application for which the invention is employed. Two type of layouts are generally available. The first, illustrated in FIG. 5 is a spatially dispersed array in which each micro-electrode can be activated separately. Thus, electrodes which are required for a certain application may be turned on, while unnecessary ones may simply be turned off. The second option is a dedicated pattern which is employed for applications where known separation distances and voltages are available. In this case, the electrodes can be laid out in a fixed pattern which is known to be satisfactory for the desired application.

To use the separation matrix of the present invention as a DNA Sequencing chip, the pores of the separation matrix are first filled with a separation fluid. This may be a buffer, a buffer containing a swelling agent, or it may be a suspension of a secondary obstacle which acts in concert with the posts of the separation matrix to form a hybrid separation matrix. In general, the secondary obstacles will be a homogeously sized and distributed suspension of structures having a size on the same order as the radius of gyration of the polymers to be separated, i.e., about 0.5 to 5 times the radius of gyration. The secondary obstacles should also be compatible with the detection system used. Thus, for fluorescence detection the secondary obstacles should be transparent or translucent, with little or no fluorescence at the wavelengths of interest. Materials which can be used as secondary obstacles include monodisperse microspheres as described by Hosaka et al, *Polym. Int.* 30: 505–511 (1993) and Sanghvi et al, *J. Microencaps.* 10: 181–194 (1993), water-soluble fullerenes (C60) as described in Diederich et al., *Science* 271: 317–323 (1996), and self-assembling dendrimer as described in Newkome et al, *J. Org. Chem.* 58: 3123 (1993) and Zimmerman et al., *Science* 271: 1095–1098 (1996).

Figure 7:
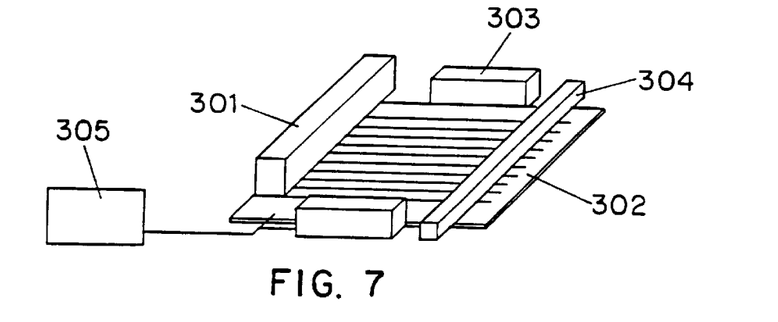
FIG. 7 shows an apparatus in accordance with the invention.

The sample to be evaluated, particularly a sample of a nucleic acid sequencing mixture prepared by the Sanger or Maxam/Gilbert methods is then loaded at one end of the separation matrix, for example in an integrated apparatus as shown schematically in FIG. 7. Preferably, a plurality of samples are loaded, one to each lane of the separation matrix.

The minimum practical loading volume, using a commercially-available micropipette, is around 100 nL (Hamilton, 1993). In contrast, a stacked electrophoresis zone 10 $\mu$m wide×1 $\mu$m deep×10 $\mu$m high (as in the entrance-way to a capillary channel of FIG. 1) will occupy a volume of 0.1 pL. Therefore a very substantial reduction in volume (up to $16^6$-fold) may be required during the initial stacking process. Such high-efficiency stacking during the initial phase of electrophoresis can be achieved with the loading device 301 shown in more detail in FIG. 8.

Figure 8:
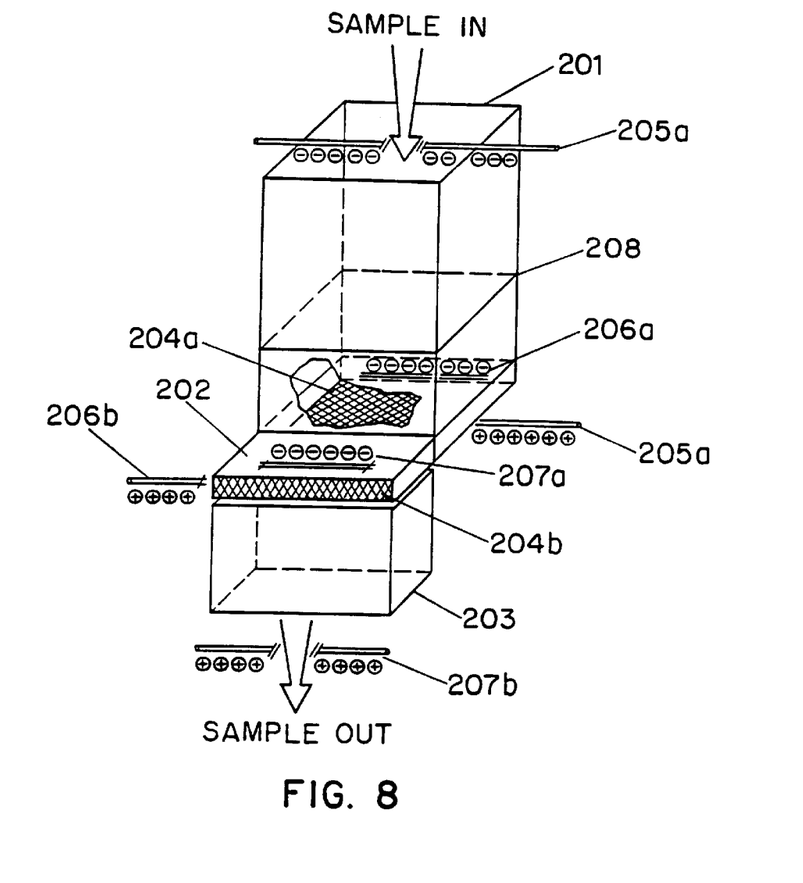
FIG. 8 shows a loading device for loading separation matrices in accordance with the invention.

The device of FIG. 8 is shown in an orientation appropriate for loading sample into a channel of a DNA sequencing chip 203 that is in the vertical orientation. The loader consists of a large rectangular channel 201 attached at right angles to a second smaller rectangular channel 202. The upper face of the large rectangular channel 201 is open, and receives a volume (for example 100 nL of unconcentrated sample containing a DNA mixture to be separated. The lower face The lower face of the smaller rectangular channel 202 is also open and releases the concentrated sample (approx 1 pL) into one of the functional channels of the DNA sequencing chip 203. There is an unrestricted passageway between the large and small channels, to allow sample to flow between them, at a time after a first concentration step and before a second concentration step.

In the first concentration step, sample loaded into the top of the large channel 202 is electrophoresed using a filed generated between electrodes 205a and 205b. The DNA is collected on a semipermeable membrane 204a which has a molecular weight cutoff low enough to prevent passage of the DNA but which permits passage of the solvent from the sample, thereby effecting a first concentration of the sample on the semi-permeable membrane 204a.

Next, a second set of electrodes 206a and 206b are turned on to generate cause the concentrated sample to migrate in a direction perpendicular to the original migration from the semi permeable membrane 204a into the small channel 202. A second semipermeable membrane 204b retains sample within the small channel 202 while permitting passage of solvent. Finally, a third electrode set 207a and 207b is used to electrophorese the doubly-concentrated sample from the small channel 202 into one of the functional channels of the DNA sequencing chip 203.

If is also possible by means of thermocouple strips 208 disposed about the periphery of the large channel 201 to achieve localized cooling of buffer in the large channel, via the Peltier effect. This strategy can be used to lower the temperature of a glycerol-containing buffer below the glass-transition temperature, thus creating a viscosity trap close to the semipermeable membrane 204a which prevents back-diffusion of concentrated DNA in the vertical direction within the large channel after the first concentration step.

It is also possible to use a simplified version of the device of FIG. 8, in which only a single stacking operation is employed. This simplified device consists of channel 201, semipermeable membrane 204a, electrode sets 205a and 205b, and 206a and 206b, and optionally the Peltier strips 208. Electrode set 206a and 206b causes the concentrated sample to be electrophoresed directly into a DNA sequencing chip rather than into a second concentration channel.

The processes that occur during the loading operation can be summarized as follows: (1) electrophoresis along the z-dimension onto a semipermeable membrane; (2) optional trapping of sample close to the membrane with a "viscosity trap"; (3) electrophoresis in the x-direction into a second semipermeable membrane; and electrophoresis in the z-direction into a functional channel in the DNA sequencing chip.

The degree of sample concentration that can be achieved in either of the stacking steps can be calculated from the theory of equilibrium electrophoresis using the equation:

$$C(z) = C_0 e^{\sigma(z-z_0) - 2B[C(z) - C_0]}$$

where $C_0$=concentration at arbitrary reference distance ($z_0$) along the electrophoretic direction, B=second virial coefficient, and $\sigma = E \cdot [\psi/k_B T]$ where E=electric field strength (V/cm), $\psi$=apparent or effective net charge (Coulombs), $k_B$=Boltzmann's constant, and T=absolute temperature. It is apparent from this equation that an arbitrarily large degree of stacking or concentration can be achieved simply by raising the electric filed strength to a sufficiently high value.

Once the samples are loaded, an electric field is applied to the sequencing chip 302 placed within holder 303 using power supply 305 to induce migration of the sample within the separation matrix. The field may be constant, or periodic field inversions can be used in increase the resolution of the single-stranded DNA ladder bands. Current can also be applied to successive electrodes along the length of the lane, or can be applied to parallel lines of electrodes within a lane to induce two-dimensional separation within the lane.

After separation of the sample into ladder bands, the DNA is detected at a detection site. The detector 304 may be of any type, and will vary depending on the nature of the material being detected. When the sequencing reactions utilize a 5'-fluorescently labeled sequencing primer, the separated bands can be detected by fluorescence. Three alternative illumination and detection schemes are exemplary of systems which can be used.

(i) Diode laser illuminator and fibre optic/phototransistor detector (Sepaniak et al., *J. Microcolumn Separations* 1: 155–157 (1981); Foret et al., *Electrophoresis* 7: 430–432 (1986); Hirokawa et al., *J. Chromatography* 463: 39–49 (1989); U.S. Pat. No. 5,302,272).

(ii) Array of diode-laser illuminators and two-dimensional CCD detector. The design for a two-dimensional CCD array detector has been described elsewhere (U.S. Pat. Nos. 4,874, 492 and 5,061,067 which are incorporated herein by reference, Eggers et al., *BioTechniques* 17: 516–524 (1994); Lamture et al., *Nucleic Acids Res.* 22: 2121–2125 (1994)). Such a system is advantageously constituted as a fixed array, into which a board-mounted DNA sequencing chip is inserted. This separates the mass-produced and relatively inexpensive sequencing chip from the expensive detection system.

(iii) Epifluorescence Microscope and Image Intensifying Camera.

While fluorescence detection is the most common technique currently employed in analysis of DNA sequencing fragments, and thus is a preferred approach in the present invention, other detector types can be used. For example, a subject molecule labeled with a radioactive moiety may be detected with a radiation detector, such as X-Ray film or a scintillation counter. Unmodified nucleic acids may also be detected by shifting polarization of input radiation as disclosed in U.S. patent application Ser. No. 08/387,272, which application is incorporated herein by reference.

In the most general application, the invention is used to move and/or separate species of charged molecules, and in particular charged bio-molecules such as proteins and nucleic acids. Further, the instant invention may be used to purify one molecular species from a sample of mixed molecular species. The object of combining the post and pore separation matrix with closely positioned electrodes is the creation of localized very-high density electric fields in the separation matrix. These localized fields can be supported with very low energy power supplies, and are therefore energy efficient. U.S. patent application Ser. No. 08/332,577 which is incorporated herein by reference demonstrates the usefulness of high density electric fields for separating charged molecules such as nucleic acids and proteins. Nucleic acids separated under extremely high electric fields (100–400 V/cm) over localized areas (1–5 mm$^2$) can be detected and/or used by conventional detectors, biosensors and micro-reactor components. These miniature components may be located at one site, or more than one site on the apparatus.

While simple separation and detection of DNA sequencing fragments is a preferred application of the chips of the invention, the chips can also be used to perform more complicated and complete analysis. Thus, the chips of the invention can be fabricated so as to move samples from one well to another for different treatments, such as in an integrated DNA diagnostic chip.

As described in Published PCT patent applications Nos. WO 96/07761 and WO 96/01908, which are incorporated herein by reference, the most cost effective means of DNA diagnosis involves a hierarchical method of testing, wherein a series of analyses of increasing accuracy are employed to diagnose the presence or absence of genetic mutation. It is possible to integrate all the hierarchical steps on one chip, as illustrated in FIG. 9.

Figure 9:
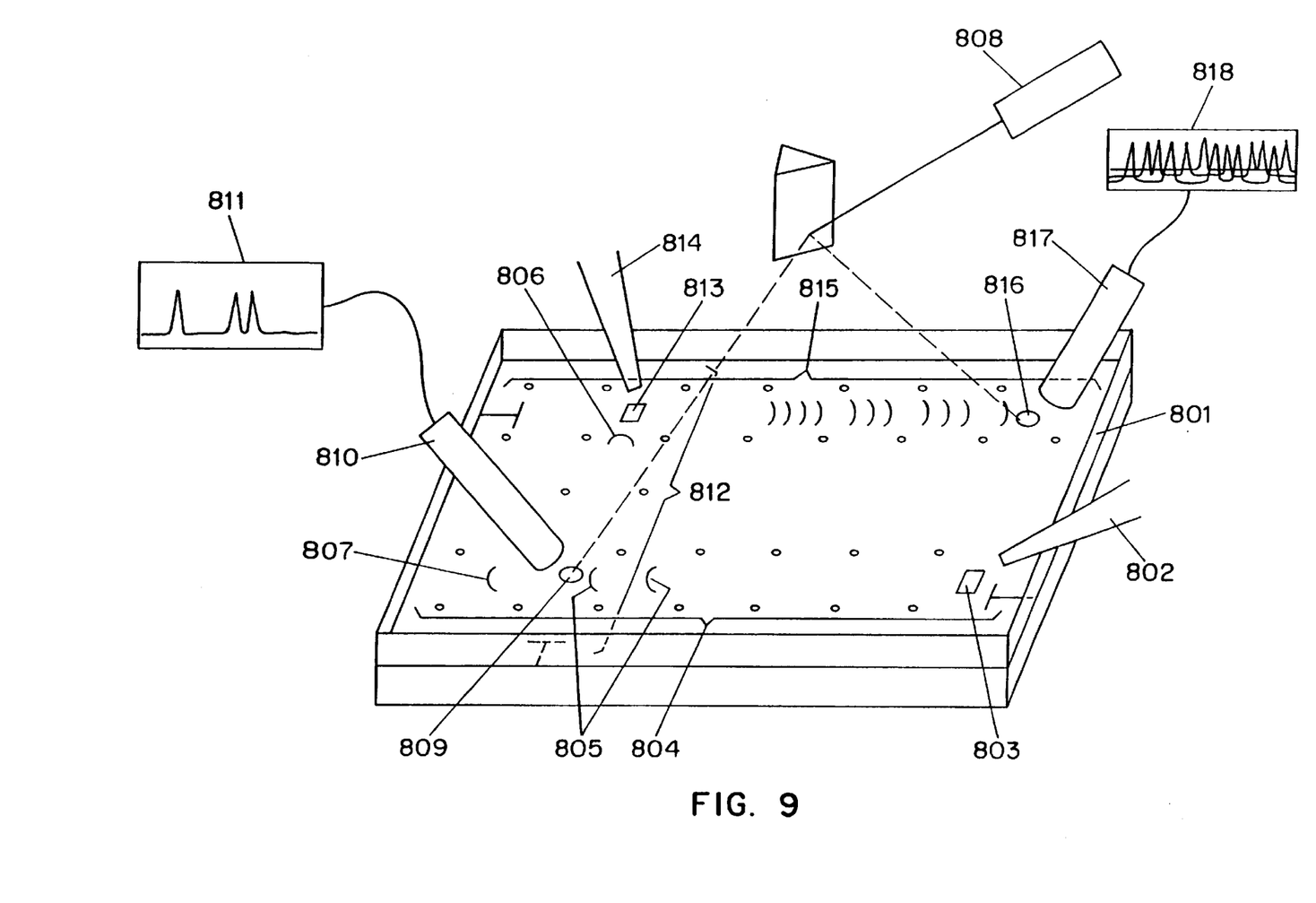
FIG. 9 shows a layout of an integrated DNA diagnostic chip in accordance with the invention.

FIG. 9 shows an integrated DNA diagnostic chip which uses the diagnostic method of the above noted patent application. A highly simplified discussion of the steps involved in the hierarchical method is provided below. In the first step, a group of exons of a gene to be diagnosed is examined for insertion and deletion mutations. In a reaction tube (not shown) the suspect exons of the patient are amplified by multiplexed PCR using oligonucleotide primers labeled with a fluorophore (not shown). The resulting fragments of DNA are loaded into the separation matrix, 801 with a loader, 802, at loading site, 803. Upon activating a group of microelectrodes, 804, the sample will migrate through the separation matrix, 801, and resolve into discrete bands of distinct species, 805, 806 and 807. A laser source, 808, of a wavelength suitable to excite the fluorophore is directed to an excitation site, 809. As a band, 806, passes through the excitation site, 809, its fluorescence emissions are detected by detector 810. The fluorescence emissions may be recorded or displayed, 811. If the band has an insertion or deletion relative to the normal gene, it will pass through the excitation zone at a time different from the expected time. Such a difference indicates the presence of a mutation in that fragment. The difference can be directly reported to the patient file. If, however, no insertion or deletion mutation is found, it is then necessary to turn to the second step of the diagnostic method, and determine the actual sequence of the DNA to determine the presence or absence of point mutations. To achieve this objective, a separated DNA fragment is moved, according to the method of the instant invention, by a series of micro-electrodes, 812 to a reaction center, 813.

Immobilized enzymes such as DNA sequencing enzymes may be located at reaction pools, as described in U.S. Pat. Nos. 4,975,175 and 5,286,364, which are incorporated herein by reference. When provided with proper reagents, which may be added by a second capillary pipettor, 814, the sequencing reaction may be carried out in situ on the diagnostic chip. After a suitable length of time, the reaction is completed. The sequenced DNA sample is then separated in a third direction by the activation of a third group of micro-electrodes, 815. The DNA sequence is obtained according to conventional fluorescence DNA sequencing: The laser source, 808, is directed to the excitation site, 816. Fluorescence emissions of the sample are recorded by a detector, 817 and recorded or displayed, 818. The presence or absence of point mutations is then recorded and reported to the patient file.

What is claimed is:

1. A separation matrix comprising a substrate having disposed on a first major surface thereof a plurality of posts, said posts being arranged at regular intervals in a plurality of parallel lines, wherein the interval between adjacent posts in a line is 100 nm or less, characterized in that the area between the posts is filled with a secondary obstacle which increases the challenge posed to a charged molecule migrating through the matrix.

2. The separation matrix according to claim 1, wherein the interval between adjacent posts in a line is 30 nm or less.

3. The separation matrix according to claim 1, wherein the posts are divided into a plurality of lanes orthogonal to the parallel lines, each lane being separated from adjacent lanes by a region of substrate having no posts thereon.

4. A chip for electrophoretic separation of charged polymers comprising
 (a) a substrate;
 (b) a plurality of posts, said posts being arranged at regular intervals in a plurality of parallel lines on a first major surface of the substrate, wherein the interval between adjacent posts in a line is 100 nm or less; and
 (c) at least two electrodes disposed on the substrate to make electrical contact with a liquid medium disposed in an area surrounding the posts for inducing an electric field for the electrophoretic separation of charged polymers, characterized in that the area between the posts is filled with a secondary obstacle which increases the challenge posed to a charged molecule migrating through the matrix.

5. The chip according to claim 4, wherein the interval between adjacent posts in a line is 30 nm or less.

6. The chip according to claim 4, wherein the posts are divided into a plurality of lanes orthogonal to the parallel lines, each lane being separated from adjacent lanes by a region of substrate having no posts thereon.

7. The chip according to claim 4, wherein an X-Y array of electrodes is disposed on the substrate.

8. A method for separating a mixture containing a plurality of species of biopolymers into subclasses of biopolymers comprising the steps of loading the mixture onto a separation matrix and applying an electric field to cause charged biopolymers in the mixture to migrate and be separated, wherein the separation matrix is a chip comprising a substrate having disposed on a first major surface thereof a plurality of posts, said posts being arranged at regular intervals in a plurality of parallel lines, wherein the interval between adjacent posts in a line is 100 nm or less, characterized in that the area between the posts is filled with a secondary obstacle which increases the challenge posed to a charged molecule migrating through the matrix.

9. The method according to claim 8, further comprising the step of detecting the separated biopolymers within the chip.

10. The method according to claim 9, wherein the separated biopolymers are detected using a fluorescence detector.

11. A method for sequencing nucleic acids comprising the steps of loading a mixture containing products from a sequencing reaction onto a separation matrix, applying an electric field to cause the products from the sequencing reaction in the mixture to migrate and be separated, and detecting separated bands of sequencing reaction products, wherein the separation matrix is a chip comprising a substrate having disposed on a first major surface thereof a plurality of posts, said posts being arranged at regular intervals in a plurality of parallel lines, wherein the interval between adjacent posts in a line is 100 nm or less, characterized in that the area between the posts is filled with a secondary obstacle which increases the challenge posed to a charged molecule migrating through the matrix.

12. The method according to claim 11, wherein the separated bands are detected using a fluorescence detector.

13. An apparatus for separation of plurality of species of biopolymers into subclasses of biopolymers comprising
 (a) a holder for receiving a chip for electrophoretic separation of charged polymers, said chip comprising
  (1) a substrate;
  (2) a plurality of posts, said posts being arranged at regular intervals in a plurality of parallel lines on a first major surface of the substrate, wherein the interval between adjacent posts in a line is 100 nm or less; and
  (3) at least two electrodes disposed on the substrate to make electrical contact with a liquid medium disposed in an area surrounding the posts for inducing an electric field for the electrophoretic separation of charged polymers, said chip having a fluid medium contained in the area between the posts; and
 (b) a power supply for applying an electric field to the chip to cause charged biopolymers in the mixture to migrate within the chip and be separated, characterized in that the apparatus further comprises a loader for decreasing the volume of a sample to be loaded onto a chip disposed within the holder.

14. The apparatus according to claim 13, further comprising a detection system for detecting charged separated biopolymers within a chip disposed in the holder.

15. The apparatus according to claim 14, wherein the detection system is a fluorescence detection system.

16. An apparatus for use in a method for sequencing nucleic acids, comprising
 a separation matrix in the form of a chip comprising a substrate having disposed on a first major surface thereof a plurality of posts, said posts being arranged at regular intervals in a plurality of lines, wherein the interval between adjacent posts in a line is 100 nm or less, characterized in that the area between the posts is filled with a secondary obstacle which increases the challenge posed to a charged molecule migrating through the matrix;
 at least two electrodes disposed on the surface to make electrical contact with a liquid medium disposed in an area surrounding the posts for inducing an electric field for the separation of charged polymers;
 a power supply for applying an electric field to the chip; and
 a loader for loading a sample onto the separation matrix, wherein the loader comprises a first concentration channel, a first pair of electrodes, a first semipermeable membrane effective to retain polynucleotide fragments while allowing passage of smaller molecules, and a second pair of electrodes, wherein the first semipermeable membrane is located between the first pair of electrodes whereby polynucleotide fragments migrating in a first electric field generated within the first concentration channel between the first pair of electrodes are retained on the first semipermeable membrane, and wherein the second pair of electrodes generate a second electric field perpendicular to the first electric field for migrating the retained polynucleotide fragments from the first semipermeable membrane.

17. The apparatus according to claim 16, further comprising a second concentration channel, a second semipermeable membrane effective to retain the biopolymers while allowing passage of smaller molecules, and a third pair of electrodes, said second pair of electrodes causing the retained biopolymers to migrate from the first semipermeable membrane through the second concentration channel to the second semipermeable membrane, and said third set of electrodes generating a third electric field perpendicular to the second electric field for migrating retained biopolymer from the second semipermeable membrane.

18. The apparatus according to claim 16, further comprising means for lowering the temperature in a portion of the first concentration channel to form a viscosity trap.

19. The apparatus according to claim 18, wherein the means for lowering the temperature in a portion of the first concentration channel is a thermocouple strip.

20. An apparatus for separation of plurality of species of biopolymers into subclasses of biopolymers comprising:
   (a) a holder for receiving a chip for electrophoretic separation of charged polymers, said chip comprising
      (1) a substrate;
      (2) a plurality of posts, said posts being arranged at regular intervals in a plurality of parallel lines on a first major surface of the substrate, wherein the interval between adjacent posts in a line is 100 nm or less; and
      (3) at least two electrodes disposed on the substrate to make electrical contact with a liquid medium disposed in an area surrounding the posts for inducing an electric field for the electrophoretic separation of charged polymers, said chip having a fluid medium contained in the area between the posts; and
   (b) a power supply for applying an electric field to the chip to cause charged biopolymers in the mixture to migrate within the chip and be separated, and
   (c) means for receiving a sample, decreasing the volume of the sample to increase the concentration of the biopolymers in the sample and loading the concentrated sample onto the chip.

21. The apparatus according to claim 20, further comprising a detection system for detecting separated biopolymers within a chip disposed in the holder.

22. The apparatus according to claim 21, wherein the detection system is a fluorescence detection system.

* * * * *